United States Patent
King et al.

(10) Patent No.: US 10,214,626 B2
(45) Date of Patent: Feb. 26, 2019

(54) RENEWABLE CROSS-LINKER FOR INCREASED BIO-CONTENT FROM FRUCTOSE

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/374,314

(22) Filed: Dec. 9, 2016

(65) Prior Publication Data

US 2018/0163016 A1 Jun. 14, 2018

(51) Int. Cl.
| | |
|---|---|
| C08K 5/17 | (2006.01) |
| C08K 5/00 | (2006.01) |
| C07D 307/66 | (2006.01) |
| C07D 307/68 | (2006.01) |
| C07D 307/42 | (2006.01) |
| C08K 5/1535 | (2006.01) |
| C08K 5/378 | (2006.01) |
| C08K 5/5435 | (2006.01) |

(52) U.S. Cl.
CPC .......... *C08K 5/0025* (2013.01); *C07D 307/42* (2013.01); *C07D 307/66* (2013.01); *C07D 307/68* (2013.01); *C08K 5/1535* (2013.01); *C08K 5/17* (2013.01); *C08K 5/378* (2013.01); *C08K 5/5435* (2013.01)

(58) Field of Classification Search
CPC .................................................. C07D 407/04
See application file for complete search history.

(56) References Cited

U.S. PATENT DOCUMENTS

| | | |
|---|---|---|
| 6,150,436 A | 11/2000 | Kastl et al. |
| 7,638,592 B2 | 12/2009 | Benecke et al. |
| 8,309,676 B2 | 11/2012 | Benecke et al. |
| 8,378,056 B2 | 2/2013 | Benecke et al. |
| 2007/0295398 A1 | 12/2007 | On Too et al. |
| 2008/0182944 A1* | 7/2008 | Benecke .............. C07D 307/34 525/410 |
| 2012/0215028 A1 | 8/2012 | Garbark et al. |
| 2012/0316307 A1 | 12/2012 | Benecke et al. |
| 2016/0167279 A1 | 6/2016 | Besson et al. |

FOREIGN PATENT DOCUMENTS

| | | |
|---|---|---|
| CN | 105658612 A | 6/2016 |
| WO | 2015031907 A1 | 3/2015 |

OTHER PUBLICATIONS

Luo, J. Org. Chem. 1999, 64, p. 1738-1740. (Year: 1999).*
Jeevanandam, J. Org. Chem. 2001, 66, p. 6014-6020 (Year: 2001).*
Fabian M. Piller and Paul Knochel, "Regio- and Chemoselective Synthesis of Fully Substituted Furans," Synthesis 2011, No. 11, pp. 1751-1758, dated Oct. 5, 2011.
Dupont Industrial Biosciences (Dupont) and Archer Daniel Midland Company (ADM), Press Release, "Opens Up Vast Landscape of Bio-Based Materials Offerings," dated Jan. 19, 2016. http://www.dupont.com/products-and-services/industrial-biotechnology/press-releases/dupont-adm-announce-plafform-technology-for-long-sought-after-molecule.html.

* cited by examiner

*Primary Examiner* — Robert C Boyle
(74) *Attorney, Agent, or Firm* — Patterson + Sheridan, LLP

(57) ABSTRACT

A class of bio-based bifuran cross-linkers are disclosed. Polymers cross-linked using the cross-linkers are also disclosed.

8 Claims, No Drawings

RENEWABLE CROSS-LINKER FOR INCREASED BIO-CONTENT FROM FRUCTOSE

BACKGROUND

Apparatus and methods described herein relate to cross-linkers derived from renewable sources. Such cross-linkers can be used to build molecular weight in polymers in a way that preserves and promotes renewable and bio-content without sacrificing the physical properties of the polymers.

Conventional methods of boosting bio and renewable content in polymers generally rely on adding polymers derived from renewable or bio-sources to petroleum-based polymers to form a mixture. Such methods generally do not link the bio-based polymers to the petroleum-based polymers chemically, or use cross-linkers that are themselves petroleum-based. Cross-linkers derived from biological or renewable sources are needed to improve the physical properties of bio-based polymers.

SUMMARY

Embodiments described herein provide a composition comprising a compound having the general structure:

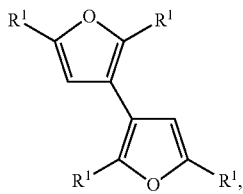

wherein $R^1$ is an organic or hetero-organic functional group.

Other embodiments described herein provide a polymer composition comprising a plurality of polymer chains linked by one or more bio-based tetrafunctional bifuran cross-linkers.

Other embodiments described herein provide a method of making a functional compound, comprising dimerizing a furan dicarboxylic ester at the 3 position.

Other embodiments described herein provide a method of making a polymer, comprising forming a mixture comprising one or more polymers from the group consisting of vinyl polymer, polyester, polyether, polyurethane, polyamine, polyamide, polyacid, polythioether, polythioamide, polythionamide, nylon, polysulfone, and polysiloxane; and adding one or more cross-linkers having the general structure

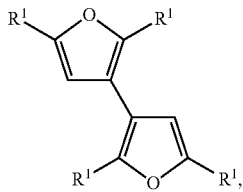

wherein $R^1$ is an organic or hetero-organic functional group.

DETAILED DESCRIPTION

Chemical structures are presented herein using a shorthand linear notation where more specific structural information is not needed to fully disclose the chemical formula. In the linear notation, atoms in the linear formula are understood to be bonded to their nearest neighbors. Thus, the linear formula ABC means A bonded to B, which is bonded to C. Subscripts may be used in the normal fashion for chemical formulas. The linear notation may include atom groups in parentheses. The parenthetical notation means that the first atom on the left in the parentheses is the anchor atom of the group, and is bonded to the nearest atoms outside the parentheses. Other atoms in the atom group inside the parentheses are understood to be bonded according to the "nearest neighbors rule". Thus, the linear formula A(BXY)C means that A is bonded to B, which is bonded to C, while X is also bonded to B and Y is bonded to X, and neither X nor Y is directly bonded to C. Neighboring parenthetical atom groups mean the anchor atoms of the groups are bonded. Thus, the linear formula A(BX)(CY)D means A is bonded to B, B is bonded to C, and C is bonded to D, while X is bonded to B and Y is bonded to C. Nested parenthetical atom groups follow the same parenthetical convention described above. When the linear formula is a formula for a radical that is bonded to some other chemical structure, the first atom on the left in the formula is the atom bonded to the other chemical structure, and radical symbols such as R, Z, X, Q, etc., potentially with identifying superscripts, may stand for atom groups with the same effect as the parenthetical notation.

The chemical structures in this disclosure may denote atomic composition of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers of the represented compounds.

Numbered chemical structures are numbered using numbers, or numbers and letters, in parentheses. Numbered chemical reaction schemes are numbered using numbers, or numbers and letters, in square brackets. Unless otherwise noted, chemical reactions are performed at ambient conditions or under slight heating with no special atmosphere or head space, and may be performed using standard organic solvents to manage mix properties such as viscosity and flow index.

The inventors have made a new class of molecules that can be advantageously used as bio-based cross-linkers for polymers, including bio-based polymers. The methods and compositions described herein are useful for tuning the physical properties of entirely bio-based polymers, or any polymer capable of reactive cross-linking.

The molecules usable as cross-linkers are tetrafunctional furyl dimers made from bio-based furans such as furan dicarboxylic methyl ester (FDME, IUPAC name dimethyl 2,5-furandicarboxylate). The cross-linker molecules are functionalized furan dimers dimerized at the 3 position, and have the general structure

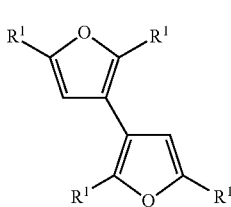

(0)

wherein $R^1$ is an organic or hetero-organic functional group, which may be selected from the group consisting of (CO)$OR^2$, (CO)OH, (CH$_2$)OH, NCO, (NH)(CO)$OR^2$, (NH)(CO)$NR^2$, NH$_2$, (CH$_2$)$_x$O$R^3$SH, (CH$_2$)$_x$O(CO)$R^3$SH (CH$_2$)$_x$O(CO)$R^3$(CH)=CH$_2$, (CH$_2$)$_x$O$R^3$(CH)=CH$_2$, and (CH$_2$)$_x$O(CO)$R^2$, or linked variations thereof, wherein $R^2$ is a functional group that has a reactive end group, such as an amine, hydroxyl, or vinyl group, $R^3$ is an organic or hetero-organic group, and x is 1 to 10. $R^2$ may include linear, cyclic, bycyclic, polycyclic, and aromatic portions along with the reactive end groups. $R^3$ may include linear, branched, cyclic, bycyclic, polycyclic, saturated, unsaturated, conjugated, and aromatic portions. One molecule of the class is tetramethyl 3,3'-bifuryl-2,2',5,5'-tetracarboxylate, also called dimethyl 2,5-furandicarboxylate, which has the structure

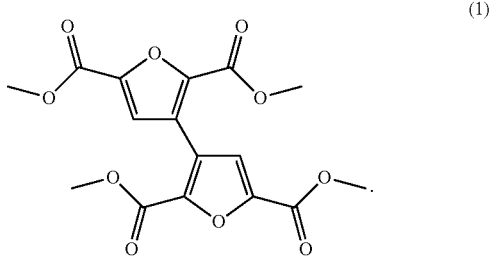

(1)

Structure (1) is available through a C—H activation reaction performed on FDME, which has the structure

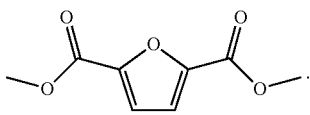

It has been reported that FDME can be made from bio-sourced fructose, so the cross-linker molecules described herein may be made from bio-sourced, and therefore renewable, materials. The C—H activation reaction is performed using 2,2,6,6-tetramethylpiperidinylmagnesium chloride:lithium chloride complex (TMPMgCl.LiCl), which is a commercially available reagent, or which can be readily synthesized from 2,2,6,6-tetramethylpiperidine and isopropylmagnesium chloride-lithium chloride. The C—H activation is followed by the addition of zinc chloride and p-chloranil to promote transmetallation, which results in the homocoupled bifuran tetraester structure (1), as shown in reaction scheme [1]:

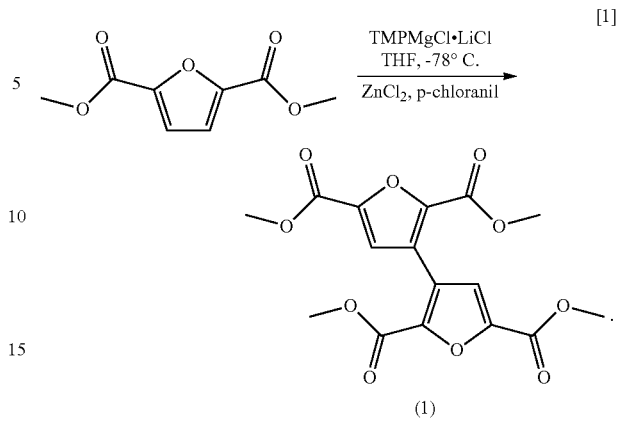

[1]

Here, THF is tetrahydrofuran and p-chloranil has the structure

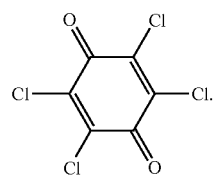 [SMILES: O=C1C(Cl)=C(Cl)C(=O)C(Cl)=C1Cl]

Derivatives of structure (1) can be made which are usable as cross-linkers by virtue of functionalization added at the methyl ester termini of structure (1). In two initial examples, structure (1) may be hydrolyzed to a tetraol ([2',5,5'-tris(hydroxymethyl)-3,3'-bifuryl-2-yl]methanol), which is structure (0) where $R^1$ is CH$_2$OH, or a tetra-acid (3,3'-bifuryl-2,2',5,5'-tetracarboxylic acid), which is structure (0) where $R^1$ is COOH, as follows:

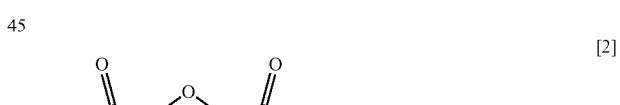

[2]

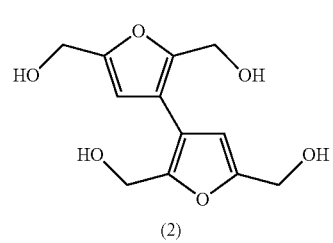

(2)

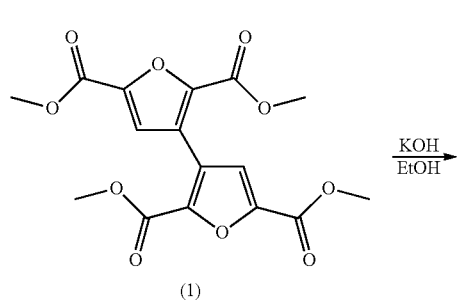

(1)

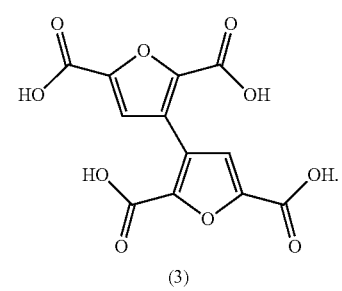

(3)

Here, Et$_2$O is diethyl ether, which functions as a solvent, and may be replaced or supplemented by any suitable organic solvent. The tetra-acid can be further cyanized through Curtius rearrangement to yield the tetraisocyanate (2,2',5,5'-tetraisocyanato-3,3'-bifuryl), which is structure (0) where R$^1$ is NCO:

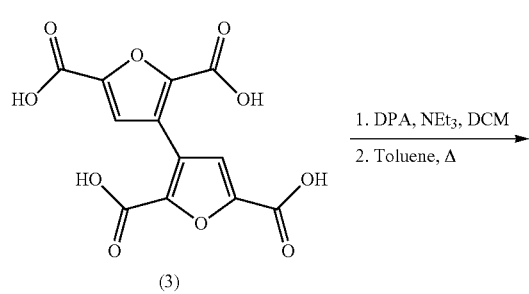

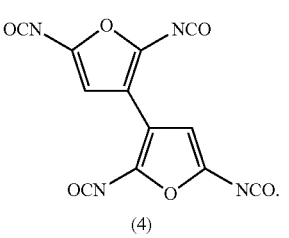

In reaction [4], DPA is diphenylamine, NEt$_3$ is triethylamine, and DCM is dichloromethane.

Further cross-linker molecules may be made from structures (2)-(4). For example, the tetraol structure (2) can yield various functionally terminated derivatives, as follows:

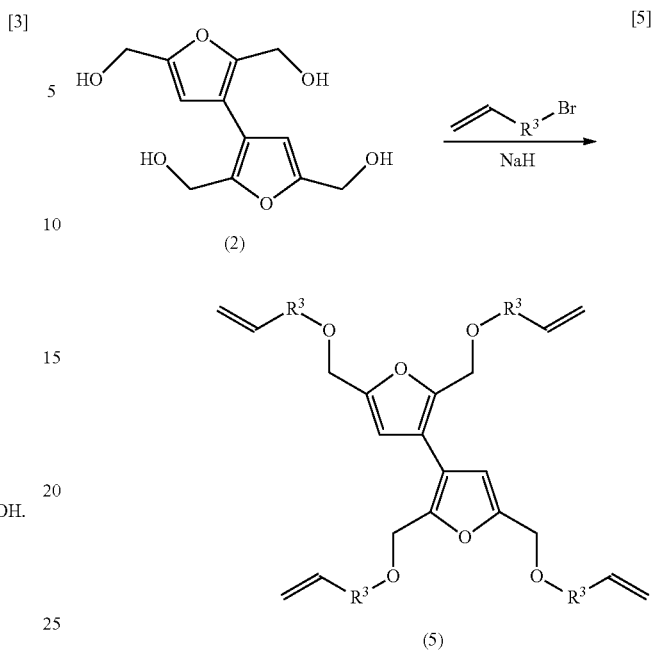

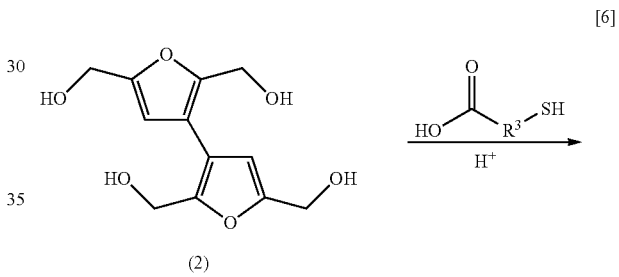

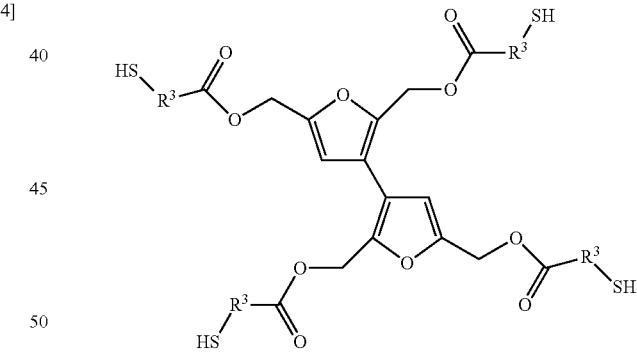

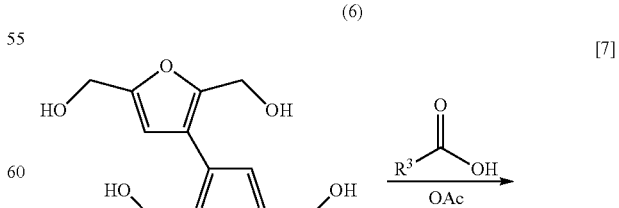

-continued
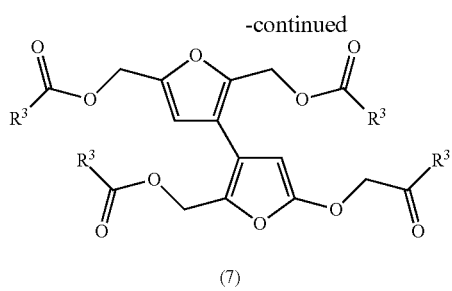
(7)
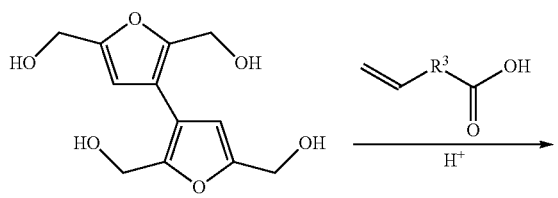
(8a)
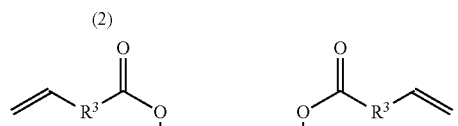
(2)
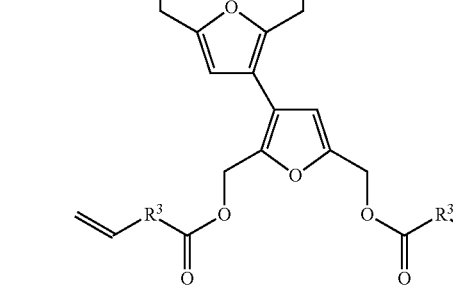
(8b)
Structures (8a) and (8b) can be used to make thiol-terminated cross-linkers, as follows:
[9a]
[9b]
Reaction schemes [8b] and [9b] are special cases of reaction schemes [8a] and [9a], respectively, where $R^3$ is just a bond. Structure (5) can similarly be transformed to a thiol-terminated cross-linker using the same reaction, as follows:
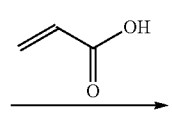
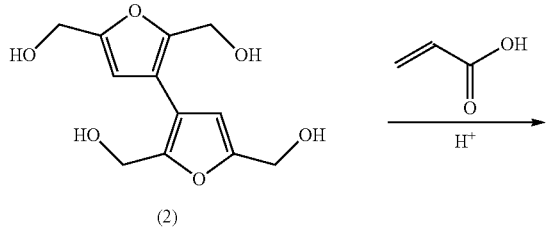
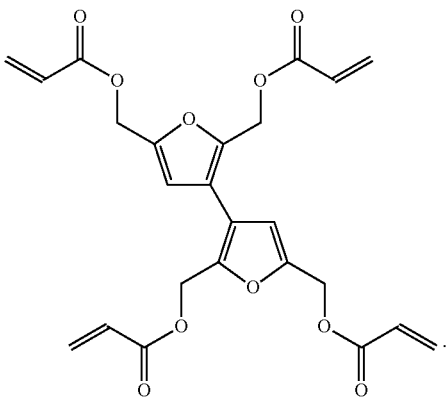

Structure (5b) can be made from structure (2) by an alkenylation reaction using an iodoalkene reagent and a copper-cesium-phenanthroline complex catalyst system, as follows:

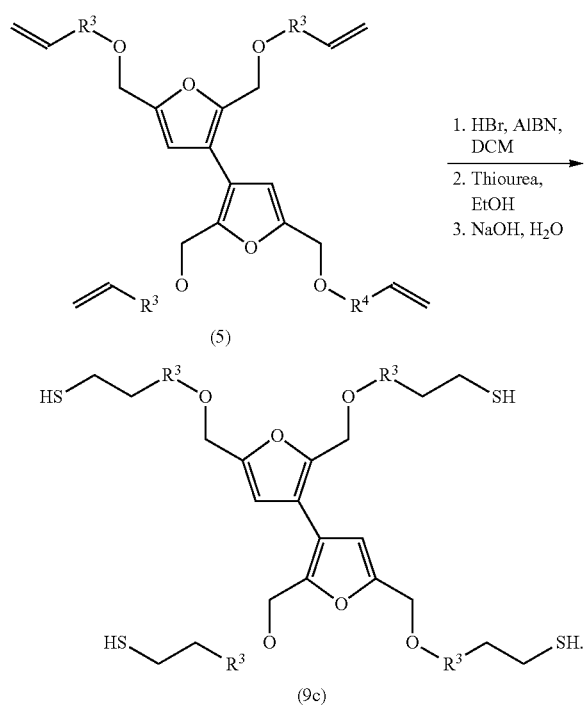

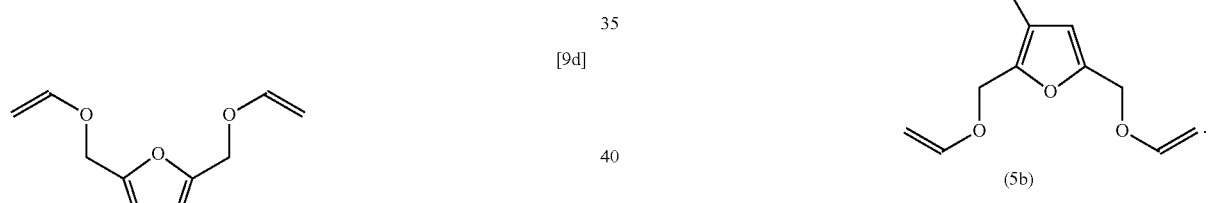

Reaction [9e] may be performed in a suitable solvent, such as toluene, by mixing the reactants and catalysts into the solvent and heating, for example to about 90° C., while stirring for a suitable length of time, such as 24 hours. Molecules of structure (5b) may be isolated by any suitable method, such as, for example, filtration on silica gel followed by flash chromatography.

To the extent the various co-reactants in reactions [4]-[9e] can be sourced from bio-based sources, the bio-based content of the various cross-linker molecules can be maximized, and a single bio-based polymer can be formed without mixing two polymers. Such a polymer can have a unimodal molecular weight distribution (for example weight-average or number-average molecular weight distribution), rather than bimodal or multi-modal distributions characteristic of mixed polymers. Exemplary co-reactants where $R^3$ is a simple alkyl group or chain include $(CH_2)=(CH)(CH_2)_xBr$ for reaction [5], $HO(CO)(CH_2)_xSH$ for reaction [6], $(CH_3)(CH_2)_x(CO)OH$ for reaction [7], and $(CH_2)=(CH)(CH_2)_x(CO)OH$ for reaction [8a], where x is generally 1 to 10.

The related scheme, where $R^3$ is just a bond, is as follows:

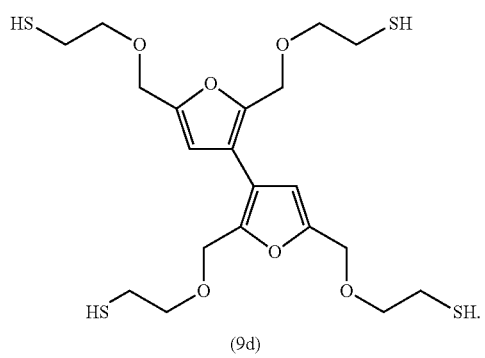

The structures above may be used to cross-link polymer chains having reactive portions that may be further reacted to form such cross-links. The polymer chains may be, or may include, vinyl polymer, polyester, polyether, polyurethane, polyamine, polyamide, polyacid, polyol, polythioether, polythioamide, polythionamide, nylon, polysulfone, polysiloxane, or a mixture thereof such as a copolymer or multipolymer thereof. The reactive portions may be primary vinyl groups, secondary vinyl groups, silanol groups, hydrosilyl groups, or $ZH_y$ groups, wherein Z is N, C, or O and y is 1 if Z is O and 2 otherwise. When cross-linking to polymer chains, the structures above adopt linked variations Structure (1) may be used as a cross-linker to bond with hydroxyl groups bonded to a polymer chain to produce a bifuryl ether cross-link, as follows:

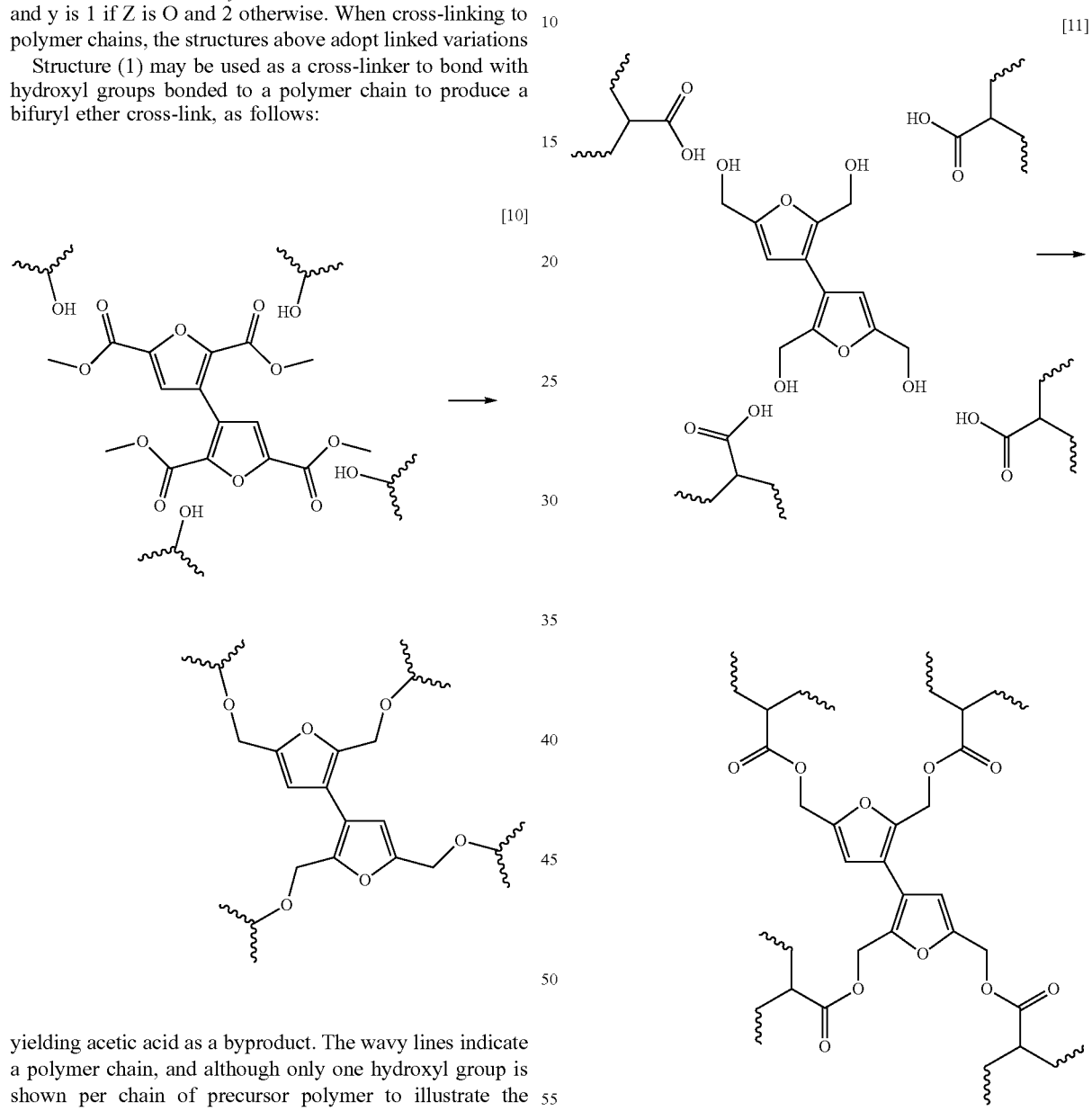

yielding acetic acid as a byproduct. The wavy lines indicate a polymer chain, and although only one hydroxyl group is shown per chain of precursor polymer to illustrate the chemical process of reaction [10], the precursor polymer may have multiple hydroxyl groups, and may thus be a polyol polymer. The precursor polymer may be a polyolefin or polymethylene, a polyacrylate, a styrenic polymer, a hydroxyl substituted polysiloxane (i.e. a silicone polymer), a polysulfone, a polyimide, a polyamide, a polylactone, a polycaprolactone, a polyurethane, a polysaccharide, or a mixture, copolymer, or multipolymer of such polymers, subject to inclusion of hydroxyl groups or substituents.

Structure (2) can be used as a cross-linker to bond with other alcohol-reactive functionalities in a polymer chain. For example, a polymer with carboxylic acid functionality, such as polyacrylic acid, or a polyalkacrylic acid such as polymethacrylic acid, can be cross-linked using the cross-linker made by reaction [2], by condensation as follows:

where the short-period wavy bonds denote bonds to extended polymer or oligomer chains. In this way, acrylic acid polymers may be cross-linked with bifuran ester linkages to form polyesters using bio-based cross-linkers. Structure (2) can also be reacted with polyisocyanates, polysiloxanes, halopolymers (see reaction [5]), and polyamines to form polyurethanes, silicones, polyethers, and polyimines having respective structures (10)-(13), as follows:

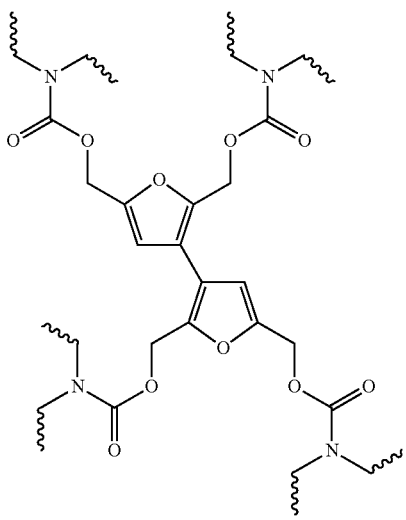
(10)

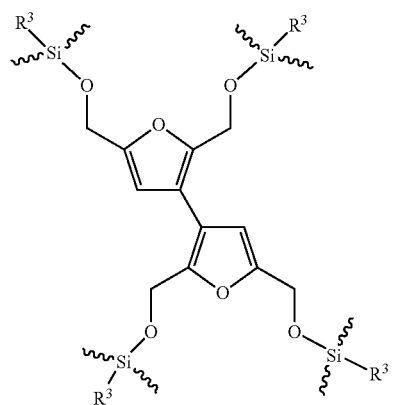
(11)

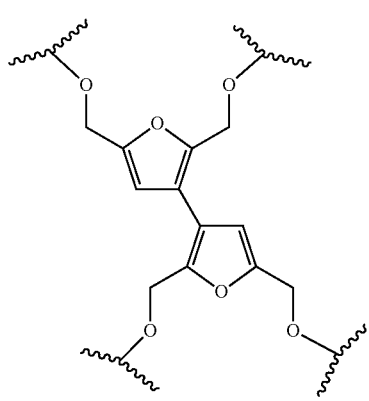
(12)

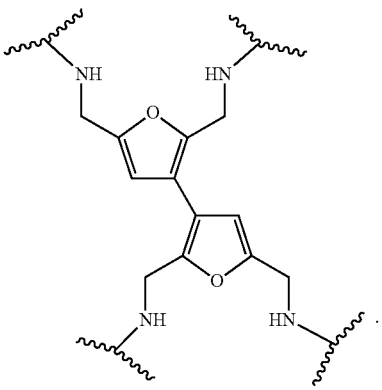
(13)

Structure (3) can be used as a cross-linker to bond with acid-reactive functionalities in a polymer chain. For example, a polymer with available hydroxyl groups, amino groups, or thiol groups can be cross-linked using the cross-linker made by reaction [3], as follows:

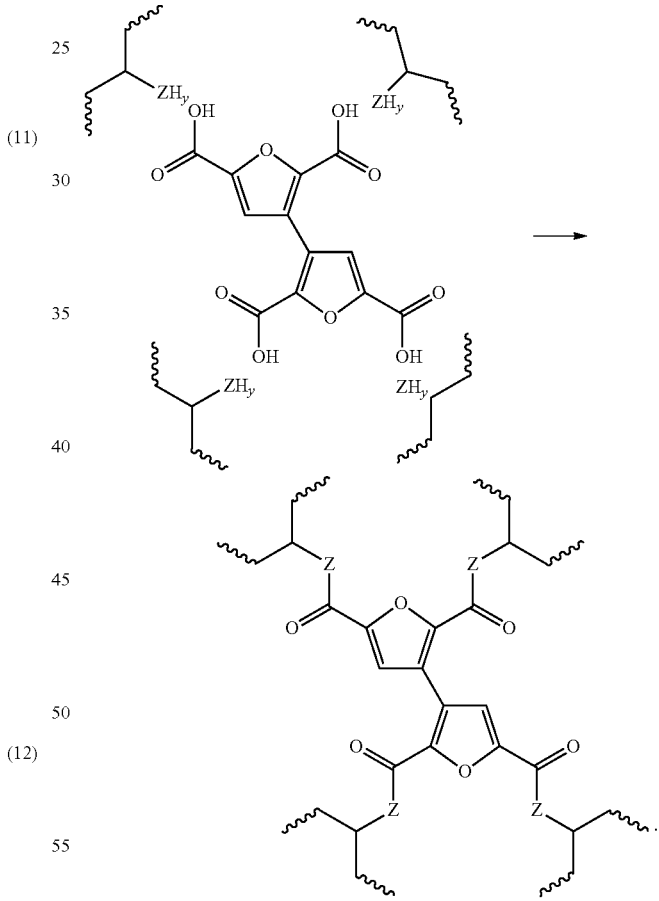

[12]

The polymer chains shown here are substituted vinyl polymers with primary $ZH_y$ functionalization, where Z is O, N, or S, and y is 1 when Z is O and 2 otherwise. When Z is O, the polymers are poly vinyl alcohols and the linkages are ester linkages, the resulting polymers being polyesters, when Z is N, the polymers are poly vinyl amines and the linkages are amide linkages, the resulting polymers being polyamides, and when Z is S, the polymers are poly vinyl thiols and the linkages are thioester linkages, the resulting polymers being polythioesters. Mixtures of such polymers may also be cross-linked using the cross-linker made by reaction [3].

The isocyanate structure (4) may be used as a cross-linker to bond with isocyanate-reactive functionality in a polymer chain. Urethane and urea linkages may be made by reacting the isocyanate functionality with alcohol and amine functionality, respectively, in polymers such as the poly vinyl polymers above. Thiourethane linkages may also be made by similar reactions with poly vinyl thiol polymers. Reaction [13] summarizes these reactions:

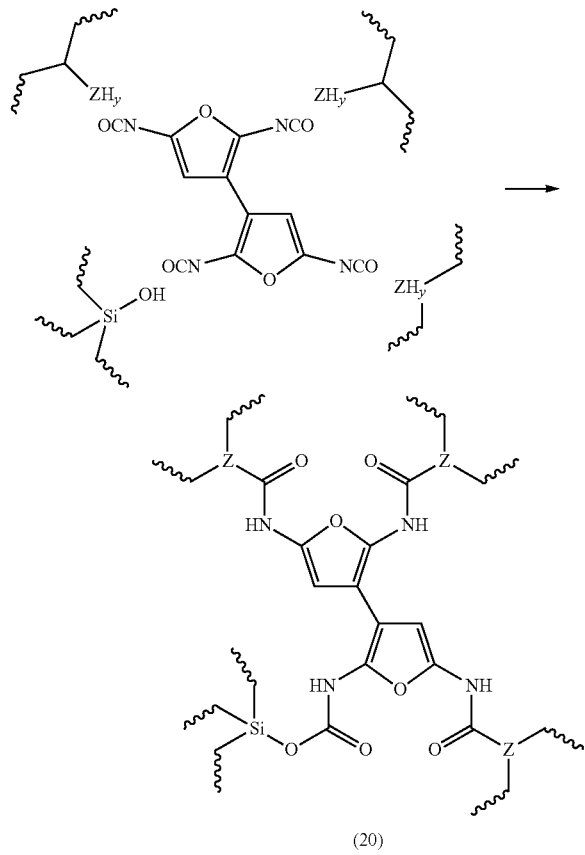

where Z is O, N, or S, as above. When Z is O, the linkages are urethane linkages and the polymers are polyurethanes. When Z is N, the linkages are urea linkages and the polymers are polyureas. When Z is S, the linkages are S-thiocarbamate linkages and the polymers are poly(S-thiocarbamates). Residual hydrogen atoms that may remain bonded to Z in the cross-linked polymers of reactions [12] and [13], when Z is N, are omitted for clarity. Note that one of the structures cross-linked in reaction [13] is a polymer having a silanol group, which reacts with the isocyanate structure in (4) to form a silylamide linkage, shown at the lower left of structure (20). Polymers resulting from such reactions are polysilylamides.

Structure (4) may also be treated with water to form an amine analogue of structure (2), as structure (21) below:

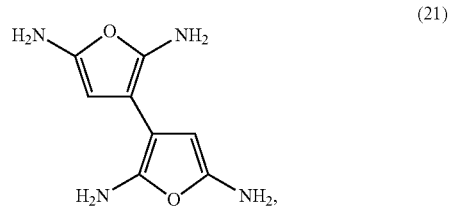 [SMILES: Nc1cc(-c2cc(N)oc2N)c(N)o1]

which is structure (1) where $R^1$ is $NH_2$. Structure (21) can participate in the standard reactions of amines with acid functionalities, for example on acrylic acid polymers to form amide linkages and polyamide polymers, and with alcohol functionalities, for example on polyols using aluminized mesoporous silica, to form aza-polymers (i.e. polymers with aza cross-linkages). Structure (21) can also participate in the standard reactions of amines with epoxides. Such reactions can be used to directly cross-link polymers having such functionalities, or to form derivative cross-linker molecules. Structure (21) has eight reactive sites that provide dense cross-linking capability, or that can be used to make cross-linkers that are octa-functionalized. With eight possible linking sites, molecules like structure (21) are more efficient cross-linkers per mole than the tetravalent varieties described above.

The thiol-terminated products of reactions [6] and [9a] can be used to cross-link primary or secondary vinyl-terminated polymer chains. Structure (6) will react with vinyl groups, as follows:

[14]

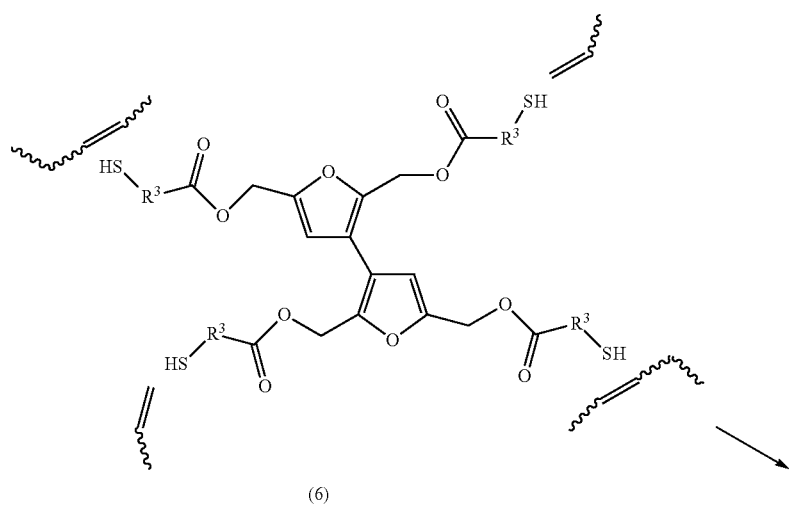

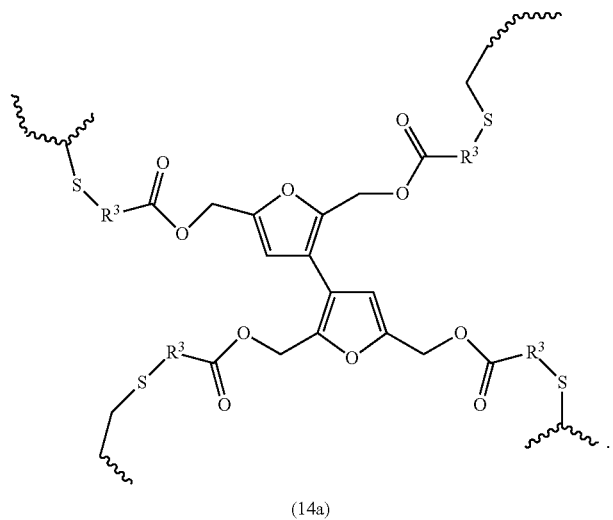

(14a)

Structure (9a) reacts similarly to form structure (14b):

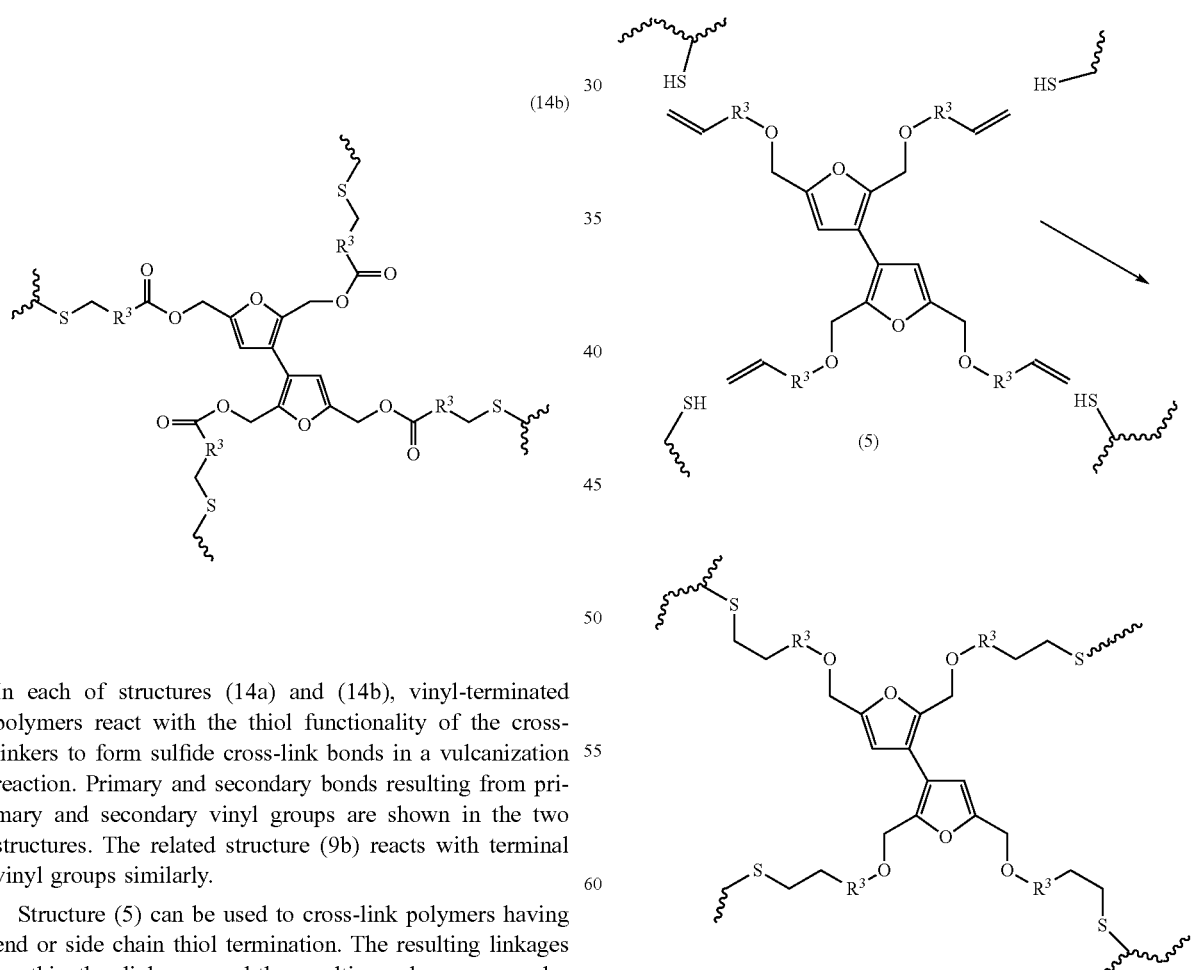

(14b)

(5)

[15]

(15)

In each of structures (14a) and (14b), vinyl-terminated polymers react with the thiol functionality of the cross-linkers to form sulfide cross-link bonds in a vulcanization reaction. Primary and secondary bonds resulting from primary and secondary vinyl groups are shown in the two structures. The related structure (9b) reacts with terminal vinyl groups similarly.

Structure (5) can be used to cross-link polymers having end or side chain thiol termination. The resulting linkages are thioether linkages, and the resulting polymers are polythioethers, as in thiol-ene click reaction [15]. Structure (5) can also cross-link polysiloxanes having hydrosilyl groups, as in hydrosilation reaction [16].

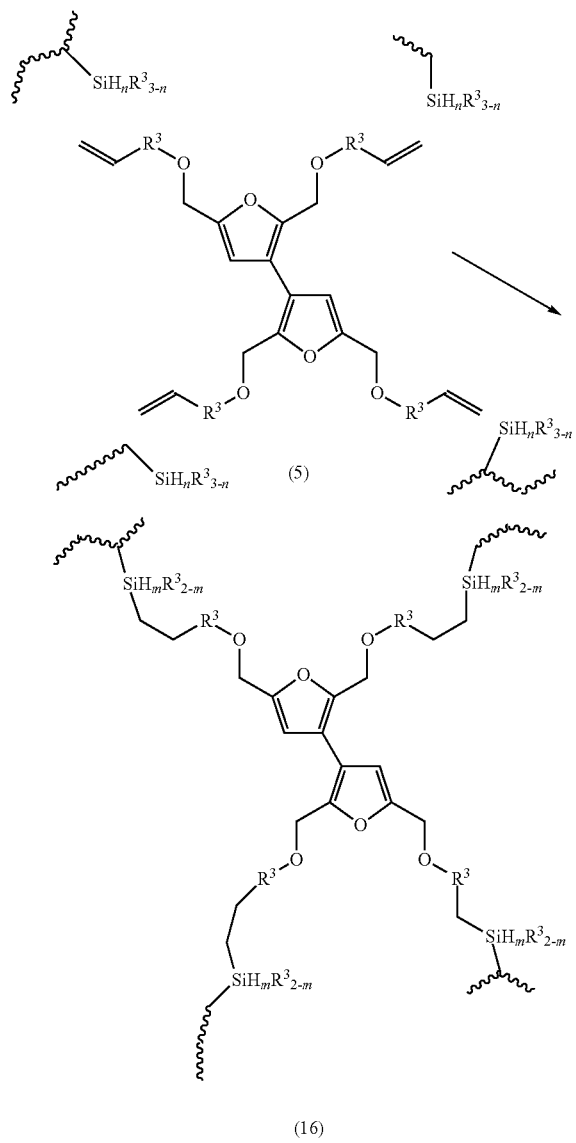

(5)

(16)

Structures (8a) and (8b) participate in similar reactions to form structures (17)-(20), as follows:

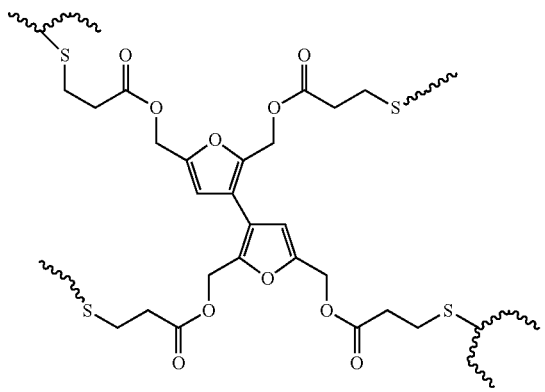

(17)

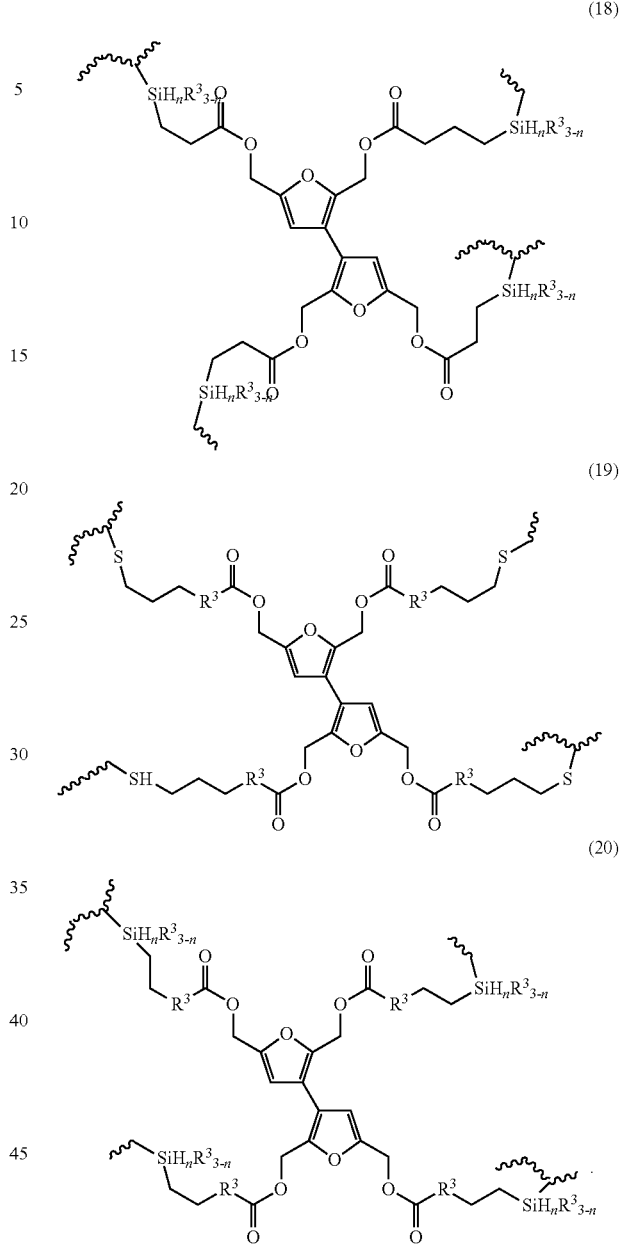

(18)

(19)

(20)

The cross-linker molecules described above (structures (1)-(9b)) can dimerize and polymerize by themselves or in copolymers or multipolymers. For example, structure (2) can copolymerize with structure (4) through Curtius rearrangement to form urethane dimers and polyurethane oligomers and polymers. Bifuran polyethers, polyesters, polyamides, polysiloxanes, polysilylamides, polyvinyls, polysulfides, polyureas, and poly(S-thiocarbamates), and block and random copolymers and multipolymers thereof, are all available through co-reaction of the various cross-linkers described above using the same chemical reactions described above.

In all the polymer cross-linking reactions shown above, it should be noted that mixtures of polymers can be cross-linked together. Such capabilities are suggested by reactions [13] and [14], where different polymers are shown reacting with a cross-linker. Any mixture of functionalized polymers that have any of the functionalities described herein could be cross-linked using the cross-linkers described herein. Further, mixtures of the different types of cross-linkers may be used to broaden the cross-linking available in a single polymer mixture. For example, alcohol- and amine-functionalized cross-linkers can be mixed with various polymers having alcohol- and amine-reactive functionalities to make random, block, or mixed multipolymers of composition and profile depending on the mix and sequence of polymers and cross-linkers.

The molecule of structure (1) is made by a method in which FMDE, which may be bio-based, is charged to a vessel containing THF/TMPMgCl:LiCl, available as a reagent from Sigma-Aldrich (CAS No. 898838-07-8), maintained at −78° C. using a cryocooler or bromobenzene/liquid $N_2$ bath. The mixture is stirred while maintaining temperature for 30 minutes. A solution of $ZnCl_2$, for example 1M $ZnCl_2$, is then added and stirring continues for 15 minutes. Then, p-chloranil is slowly added, and after stirring for 15 minutes the mixture is then warmed to −40° C. and stirred for 2 hours. The reaction mixture is then quenched with $NH_4Cl$, and the aqueous phase removed. The molecule of structure (1) may be isolated, if desired, by solvent extraction, evaporation, or replacement.

As noted herein, structure (1) is generally made from furan dicarboxylic methyl ester. Other variant esters may also be used to make analogs of structure (1) that can then be used to form cross-linker molecules as described herein. For example, esters other than the methyl ester may be used. For example, furan dicarboxylic esters having the general structure

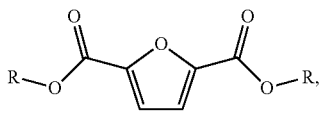

where R is any acid-reactive group (e.g. alcohol, amine, etc.) capable of condensing with a carboxylic acid, may be used. Structure (1a) results, as follows:

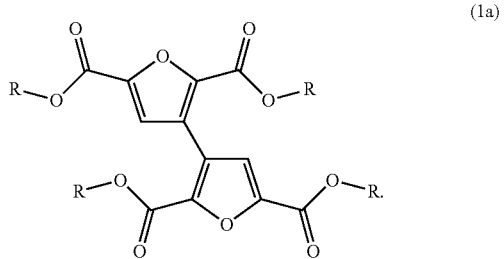

(1a)

Other derivatives of the ester above may be used as starting points. For example, the following extended furan diester structure may be used as a starting point:

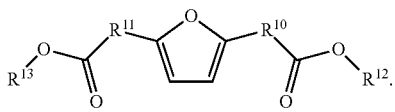

Structure (1b) results:

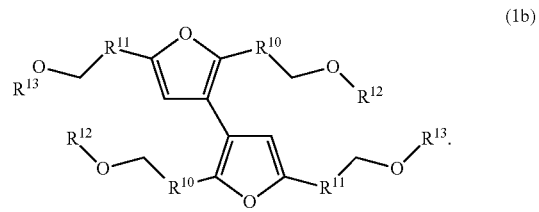

(1b)

$R^{10}$ and $R^{11}$ above are each, individually, a linking group such as an alkyl group, or any other organic or hetero-organic linking group. $R^{10}$ and $R^{11}$ are each, individually, any acid-reactive group, similar to group R above. Where $R^{10}$ and $R^{11}$ are simple methylene chains, structure (1c) results:

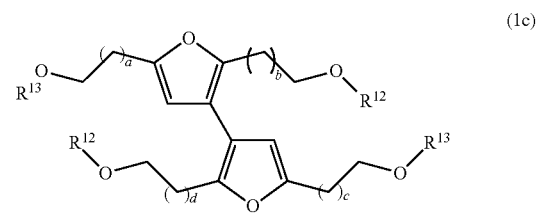

(1c)

where a, b, c, and d are integers from 1 to 10. The ester structures (1a), (1b), and (1c) participate in the array of reactions shown above for structure (1), to the extent reagents used in the reactions are not consumed, deactivated, or otherwise changed by reactions with any structures in the radical groups $R^{10}$-$R^{11}$.

While the foregoing is directed to embodiments of the present invention, other and further embodiments of the invention may be devised without departing from the basic scope thereof, and the scope thereof is determined by the claims that follow.

What is claimed is:

1. A composition comprising a compound having the general structure:

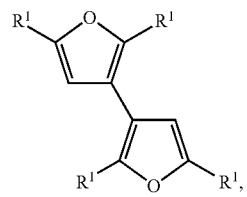

wherein:
each $R^1$ includes a hetero-organic functional group selected from the group consisting of $(CO)OR^2$, $(CO)OH$, $(CH_2)OH$, NCO, $(NH)(CO)OR^2$, $(NH)(CO)NR^2$, $NH_2$, $(CH_2)_xOR^3SH$, $(CH_2)_xO(CO)R^3(SH)$, $(CH_2)_xO(CO)R^3(CH)=CH_2$, $(CH_2)_xOR^3(CH)=CH_2$, and $(CH_2)_xO(CO)R^2$, or linked variations thereof,
when $R^1$ includes $R^2$, then $R^2$ is a functional group that has a reactive end group,
when $R^1$ includes $R^3$, then $R^3$ is an organic or hetero-organic group, and
x is 1 to 10.

2. The composition of claim 1, further comprising a cross-linkable bio-based polymer.

3. The composition of claim 2, wherein the cross-linkable bio-based polymer includes a reactive portion selected from the group consisting of $ZH_y$, primary vinyl, secondary vinyl, silanol, and hydrosilyl, wherein Z is N, C, or O, and y is 1 if Z is O and 2 otherwise.

4. The composition of claim 3, wherein the cross-linkable bio-based polymer includes vinyl polymer, polyester, polyether, polyurethane, polyamine, polyamide, polyacid, polythioether, polythioamide, polythionamide, nylon, polysulfone, polysiloxane, or a mixture thereof.

5. The composition of claim 1, wherein the compound is a cross-linker for two or more polymer chains.

6. The composition of claim 5, wherein each polymer chain includes a reactive portion selected from the group consisting of primary vinyl groups, secondary vinyl groups, silanol groups, hydrosilyl groups, or $ZH_y$ groups, wherein Z is N, C, or O, and y is 1 if Z is O, and 2 otherwise.

7. A composition comprising a compound having the general structure:

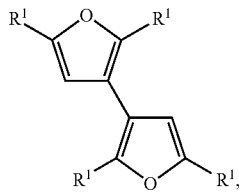

wherein $R^1$ is a hetero-organic functional group, each $R^1$ including a polymer selected from the group consisting of vinyl polymers, polyesters, polyethers, polyurethanes, polyamines, polyamides, polyacids, polythioethers, polythioamides, polythionamides, nylons, polysulfones, polysiloxanes, or mixtures thereof.

8. A composition comprising a bio-based compound having the general structure:

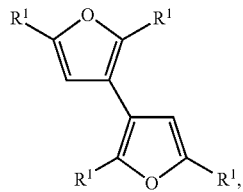

wherein:
the bio-based compound is a cross-linker for two or more polymer chains, and $R^1$ is a hetero-organic functional group linked to a furan ring of the general structure by an ether linkage, an ester linkage, an amine linkage, an amide linkage, a thioester linkage, a thiourethane linkage, or a methylene chain, and each $R^1$ includes a polymer selected from the group consisting of vinyl polymers, polyesters, polyethers, polyurethanes, polyamines, polyamides, polyacids, polythioethers, polythioamides, polythionamides, nylons, polysulfones, polysiloxanes, or mixtures thereof.

* * * * *